(12) United States Patent
Flinchbaugh

(10) Patent No.: US 6,855,126 B2
(45) Date of Patent: Feb. 15, 2005

(54) CONFORMABLE BALLOONLESS CATHETER

(75) Inventor: David E. Flinchbaugh, Orlando, FL (US)

(73) Assignee: David Flinchbaugh, Orlando, FL (US)

( * ) Notice: Subject to any disclaimer, the term of this patent is extended or adjusted under 35 U.S.C. 154(b) by 202 days.

(21) Appl. No.: 10/113,036

(22) Filed: Apr. 1, 2002

(65) Prior Publication Data

US 2002/0143292 A1 Oct. 3, 2002

Related U.S. Application Data

(63) Continuation-in-part of application No. 10/010,534, filed on Dec. 7, 2001, now Pat. No. 6,673,051.
(60) Provisional application No. 60/280,765, filed on Apr. 2, 2001, provisional application No. 60/280,766, filed on Apr. 2, 2001, provisional application No. 60/280,769, filed on Apr. 2, 2001, provisional application No. 60/284,113, filed on Apr. 2, 2001, provisional application No. 60/280,767, filed on Apr. 2, 2001, provisional application No. 60/280,768, filed on Apr. 2, 2001, and provisional application No. 60/324,601, filed on Sep. 25, 2001.

(51) Int. Cl.$^7$ ................... A61M 29/00; A61M 25/00; A61M 27/00
(52) U.S. Cl. ................... 604/106; 604/247; 604/265; 604/523; 604/537; 604/544
(58) Field of Search ................... 604/247, 264, 604/265, 523, 537, 544, 104–109

(56) References Cited

U.S. PATENT DOCUMENTS

| | | | | |
|---|---|---|---|---|
| 3,105,511 A | * | 10/1963 | Murphy Jr. | 137/399 |
| 3,397,699 A | * | 8/1968 | Kohl | 604/105 |
| 3,495,620 A | * | 2/1970 | Bazell | 137/529 |
| 3,731,670 A | * | 5/1973 | Loe | 600/30 |
| 3,758,073 A | * | 9/1973 | Schulte | 251/342 |
| 3,812,841 A | * | 5/1974 | Isaacson | 600/29 |
| 3,874,388 A | * | 4/1975 | King et al. | 606/232 |
| 4,424,058 A | * | 1/1984 | Parsons et al. | 604/118 |
| 4,585,000 A | * | 4/1986 | Hershenson | 606/194 |
| 4,705,070 A | * | 11/1987 | Eidsmore | 137/614.21 |
| 4,865,588 A | | 9/1989 | Flinchbaugh | 604/129 |
| 5,114,412 A | | 5/1992 | Flinchbaugh | 604/247 |
| 5,140,999 A | | 8/1992 | Ardito | 128/885 |
| 5,735,831 A | | 4/1998 | Johnson | 604/280 |
| 6,096,013 A | | 8/2000 | Hakky | 604/349 |
| 6,221,060 B1 | * | 4/2001 | Willard | 604/264 |
| 6,436,084 B1 | * | 8/2002 | Finch et al. | 604/506 |
| 6,451,042 B1 | * | 9/2002 | Bonutti | 606/190 |

OTHER PUBLICATIONS

McDermott, Jr. *The New England Journal of Medicine*, vol. 319, No. 6, pp. 345–346.
Wyngaarden, James B., *Cecil Textbook of Medicine*, 1988 W. B. Saunders Company, 18$^{th}$ edition, 1988, p. 628.

* cited by examiner

*Primary Examiner*—Larry I. Schwartz
*Assistant Examiner*—Michael G. Bogart
(74) *Attorney, Agent, or Firm*—Brian S. Steinberger; Law Offices of Brian S. Steinberger, P.A.

(57) ABSTRACT

Indwelling catheter having an upper distal end having a portion that can expand within a bladder type spaces without having to be inflated. An embodiment allows for at least one slit on an upper side of the catheter tube and a head member that when pulled down by a stylette moving inside the catheter causes a bulge wing portion(s) that holds the catheter safely and painlessly within the bladder. Magnetic and electret valves can be included inside the tube of the catheter that can cycle between open and closed positions when activated by normal bladder pressure when urination is desired. The novel catheter tube can naturally conform to an opening and closing urethra during natural bladder drainage. The catheter tube surface can include an anti-microbial layer that is either or both coated and impregnated thereon with either an antibacterial and/or hydrophyllic materials. Sampling ports can be located on both inside catheter tube valves and on an externally attached magnetic valve.

12 Claims, 8 Drawing Sheets

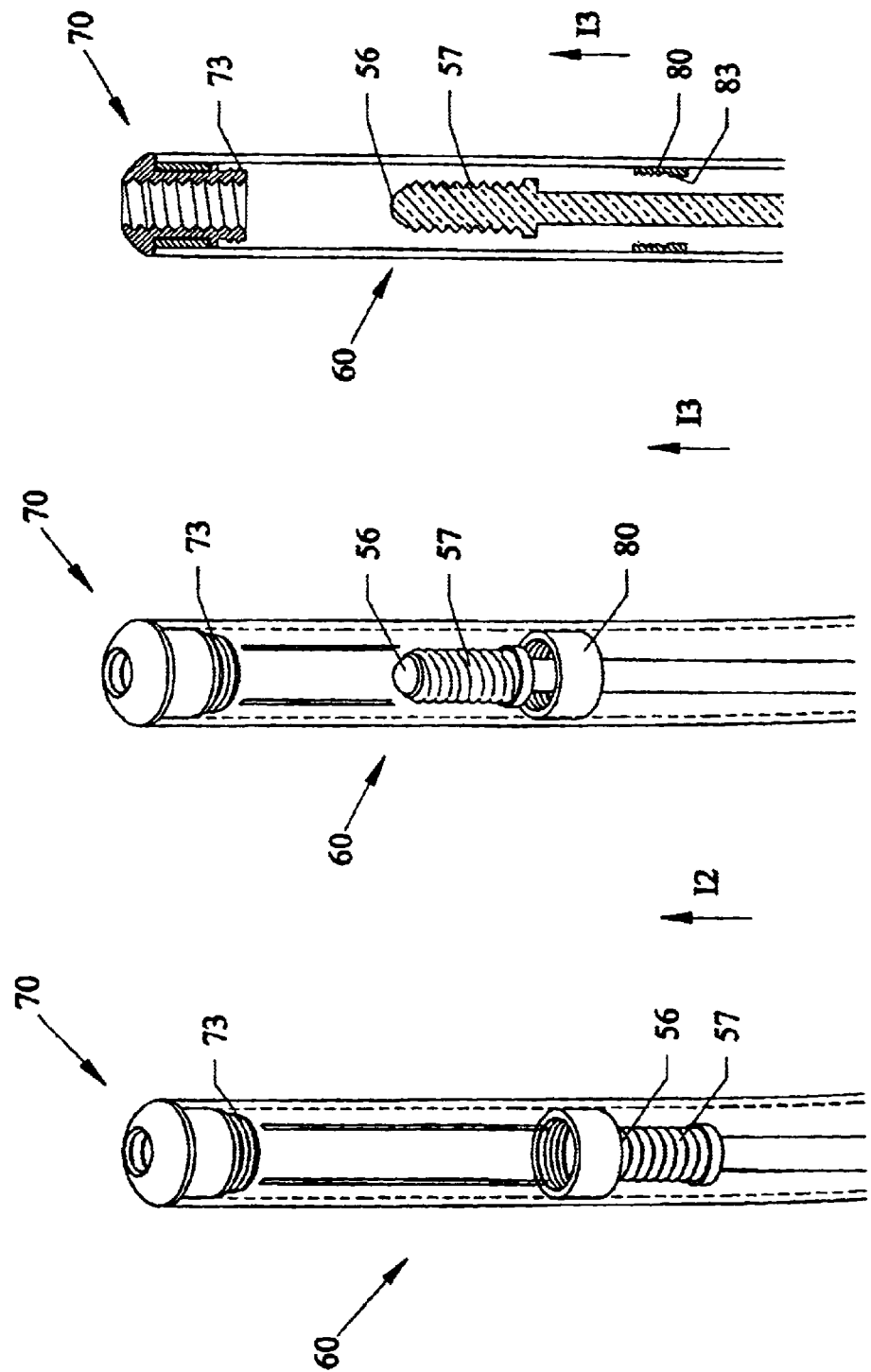

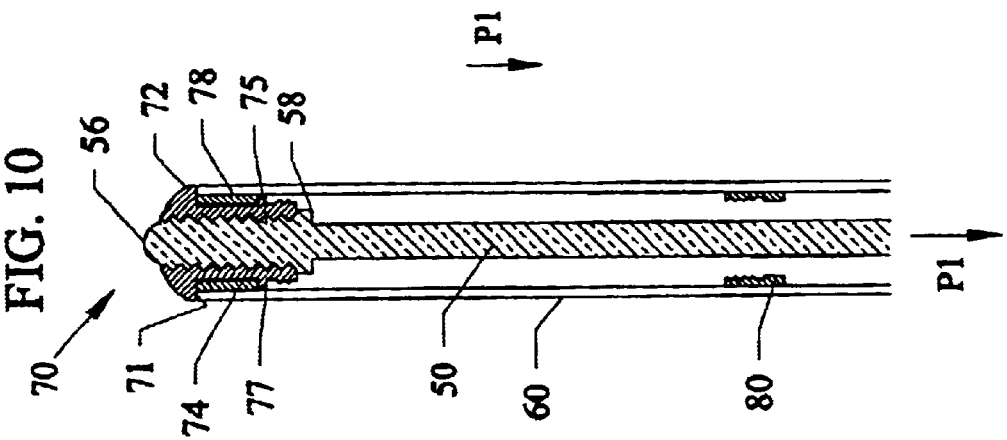
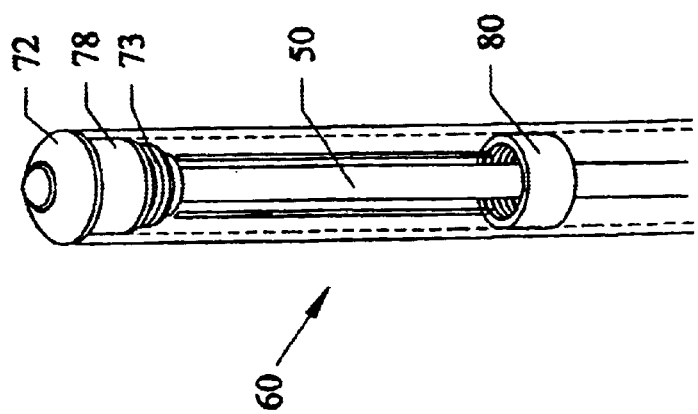
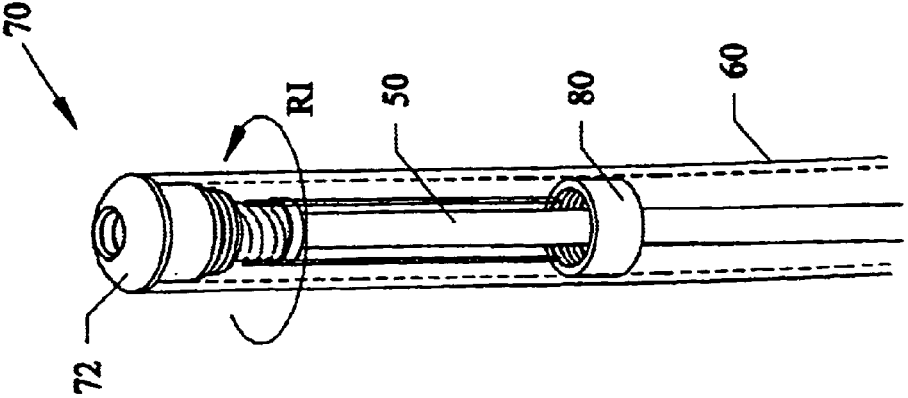

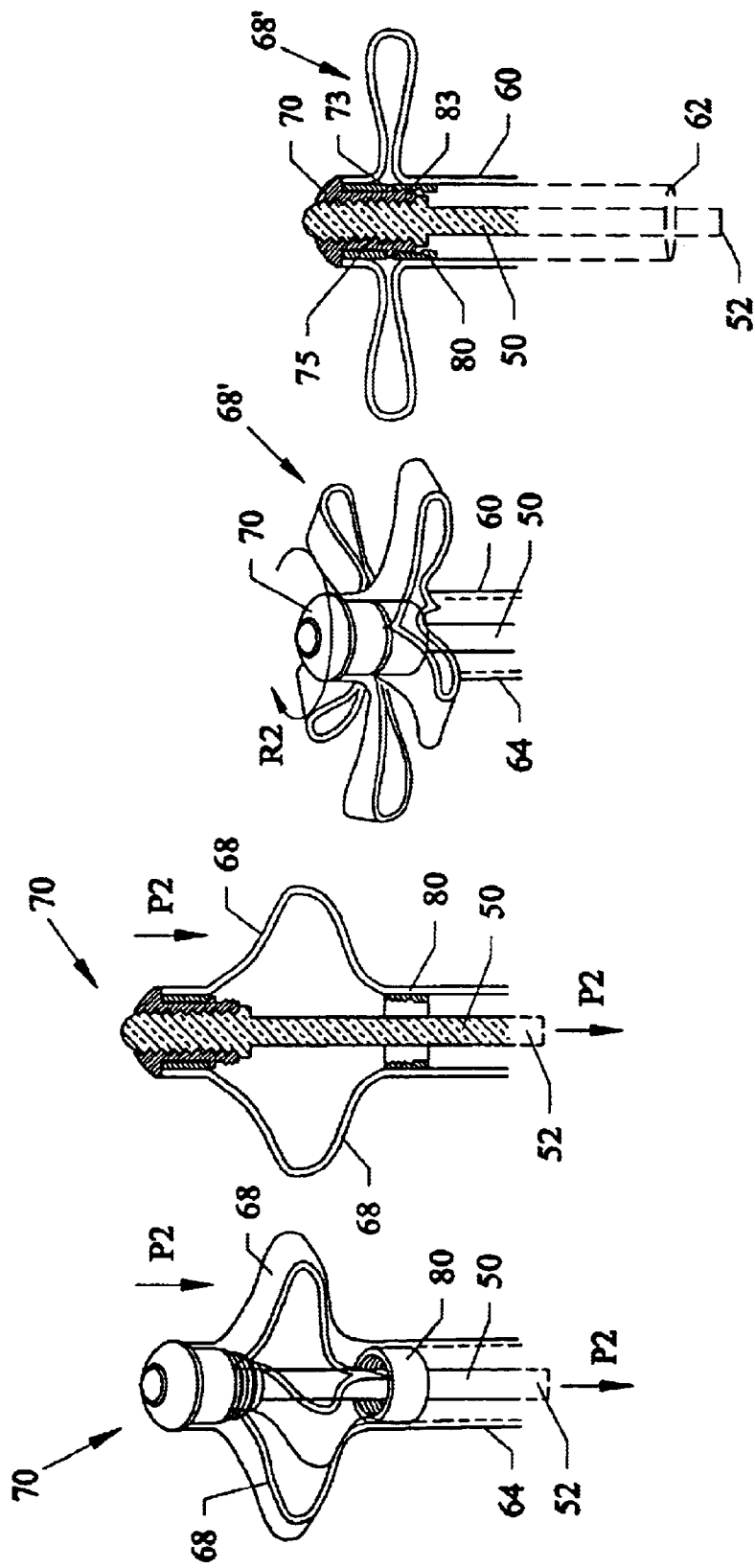

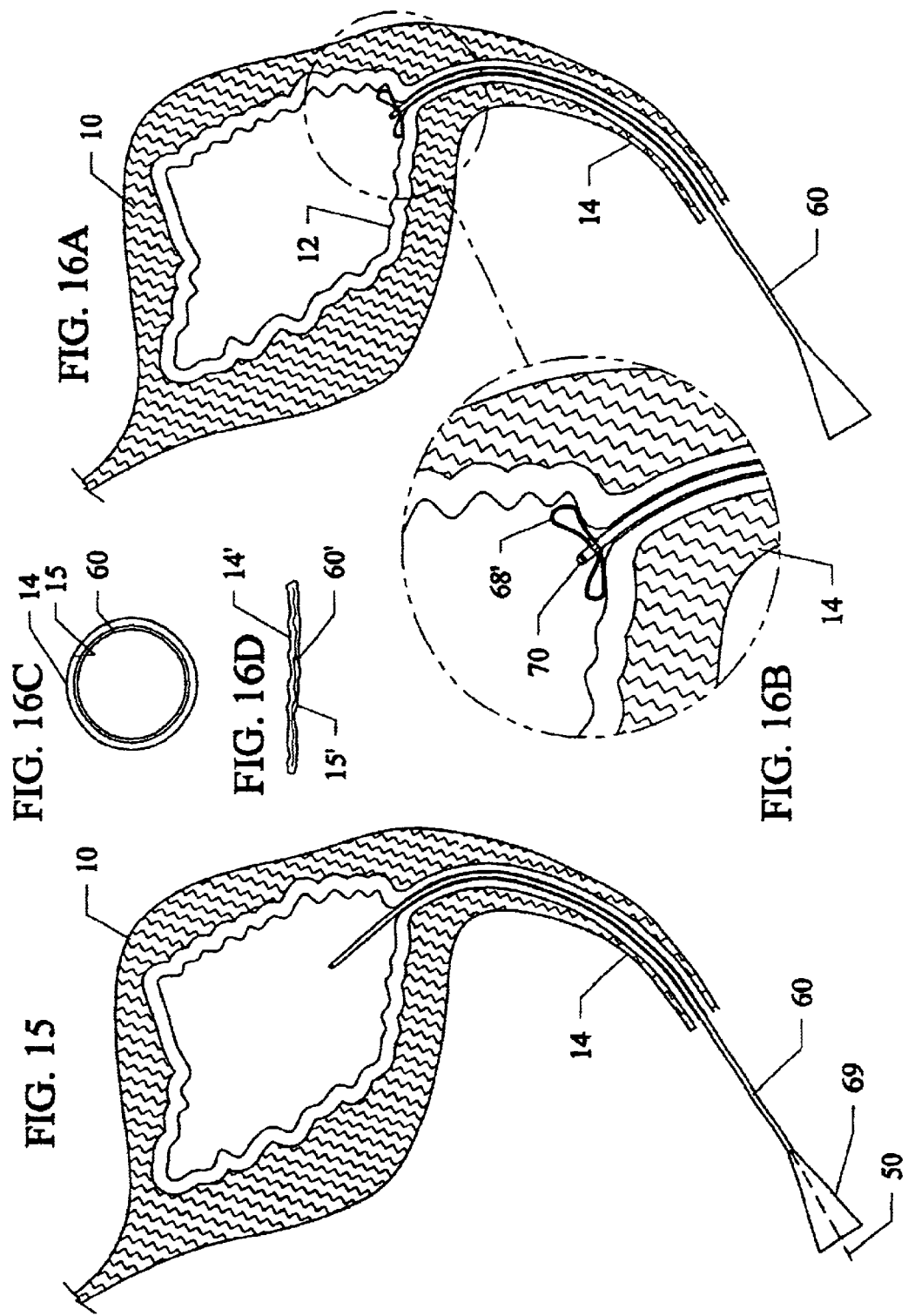

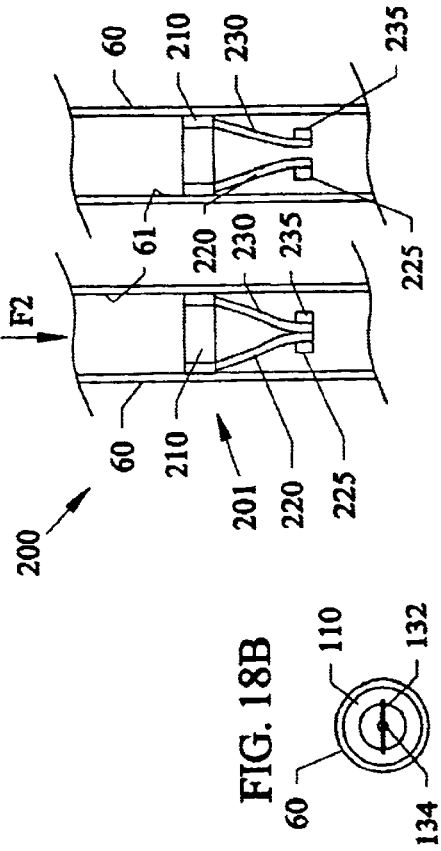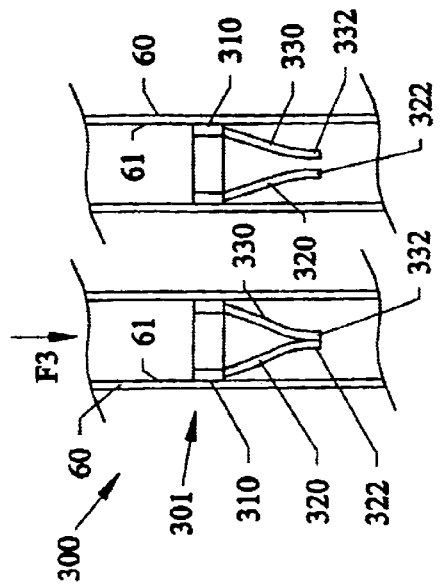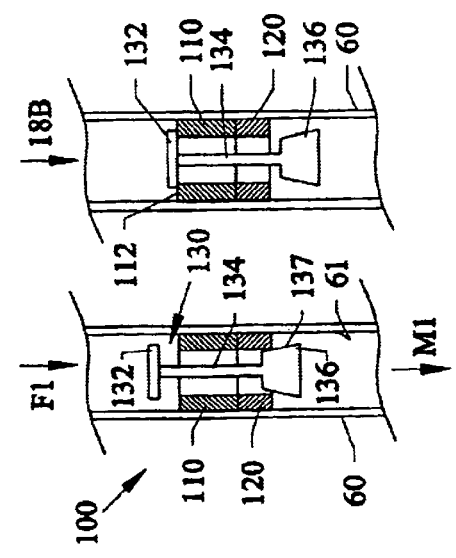

CONFORMABLE BALLOONLESS CATHETER

This invention relates to surgical devices, and in particular to methods and apparatus for attaching indwelling catheters for draining the urinary bladder that can use pressure actuated magnetic and electret valves sized to be inside catheter tubes and attached to ends of the tubes for restoring normal body cycling functions of allowing the bladder to be filled and emptied, and/or with anti-microbial surfaces, and/or sampling ports and this invention claims the benefit of priority to U.S. Provisional Application 60/280,765 filed Apr. 2, 2001, and U.S. Provisional Application 60/280,766 filed Apr. 2, 2001, and U.S. Provisional Application 60/280,769 filed Apr. 2, 2001, and U.S. Provisional Application 60/284,113 filed Apr. 2, 2001, and this invention is a Continuation-In-Part of U.S. application Ser. No. 10/010,534 filed Dec. 7, 2001, now U.S. Pat. No. 6,673,051 which claims the benefit of priority to U.S. Provisional Application 60/280,767 filed Apr. 2, 2001 and U.S. Provisional Application 60,280,768 filed Apr. 2, 2001 and U.S. Provisional Application 60/324,601 filed Sep. 25, 2001.

BACKGROUND AND PRIOR ART

Catheters are often used for performing continuous bladder irrigation. The most popular type of catheter used is a Foley indwelling or retention catheter that uses an inflatable balloon at the end being inserted into the bladder. See for example, U.S. Pat. No. 4,335,723 to Patel. For the Foley catheter a separate inflation tube adjacent to the main catheter tube or circumferential about the main catheter tube is used to inflate the balloon portion inside the bladder.

Urinary catheters bypass the normal bladder process of storing urine, and for releasing the urine by using the bladder detrusor muscle. Catheters can be a necessary tool to open the bladder to allow urination when patients have trouble urinating. A catheter can be a lifesaving tool since an uncontrolled buildup of urine can cause serious medical problems including renal(kidney) failure and death.

FIG. 1A shows a prior art indwelling Foley type catheter 1 with a balloon tipped end 3 adjacent to an interior bladder portion 12 adjacent to the urethra(neck) 14 of the bladder 10. Catheter 1 also includes a longitudinal tube portion 5 having both a main catheter line with output end 9 and a balloon inflation line 6 that feeds to an exterior valve port 7. FIG. 1B represents a cross-section of a portion inside of the urethra lining 14 having a catheter tube 5 inside the inner walls 15 thereof. A standard catheter tube 5 can have a wall thickness of approximately 1/16 of an inch, with an outer diameter of approximately 1/4 inch and a hollow inner diameter of approximately 1/8 of an inch. Along the inner wall 6 of the catheter tube 5 can be a fluid fill line 8 that is formed/located about the main drainage tube(lumen) portion 4 of the catheter tube 5. Although popular, these catheters have many problems.

In the prior art devices that use these typical catheters 5, the urethra passage 15 in the urethra always remains open to a uncontrolled, involuntary drip/drain urination whether the patient is in need of urinating or not. Thus, the typical catheter tube 5 is not capable of collapsing, and instead forces the urethra passage 15 to be maintained in a substantially open state.

The extra balloon inflation line 8 which could also be placed between 15 and 16, can also further restrict the diameter of the main catheter line thus reducing bladder drainage rate when needed. Additionally, the extra balloon inflation line 8 can require a larger insertion space diameter in the urethra passage 15 for being inserted into the bladder 10. Additionally, the Foley catheter must be stiff to be introduced into the bladder, and thus stretches the urethra 14 while being used.

The constant stretching of the passage 15 in the urethra 14 by the non-collapsible catheter tube 5 can be so painful in some patients that its' continued use cannot be tolerated. The continuous stretching of the urethra 14 can also produce urethritis and/or urinary tract infections. Often patients may need medications, sedation and sometimes narcotics to ease extremely painful bladder spasms and urethral discomfort that can develop from using the Folely catheter.

Various types of catheters have been proposed but still fail to overcome the problems of the Foley Catheter. See for example, U.S. Pat. No. : 5,183,464 to Dubrul et al.; U.S. Pat. No. 5,735,831 to Johnson et al. and U.S. Pat. No. 6,096,013 to Hakky et al. Each of these patents generally require inflatable portions or retainers having similar problems.

Catheters have also been known to cause other types of problems. Struvite crystal encrustation is the effect of stagnated urine in the neck of the bladder when using a catheter. In the face of an indwelling catheter, urine can pool at the neck of the bladder, and the pooled urine can shift from a normal acidic pH factor to an abnormal alkaline pH level of 10 or more while it stagnates. Urine shifts to an ammonia state where struvite crystals can precipitate and enlarge on the indwelling catheter. Struvite crystals have sharp, jagged edges which can seriously lacerate the urethral lining when the conventional catheter is removed. This bloody situation is not only excruciatingly painful but can lead to deadly infections. This situation can occur as the bladder loses its natural ability to cyclically flush itself in the face of an indwelling catheter. Bladder wall thickening has also been observed in long-term catheterizations and may be a result of the increasing pH levels.

Urinary tract infections can occur as the urine stagnates and shifts from its normal, acidic antibiotic property through the pH spectrum. Pooled urine that can occur in the neck of the bladder around the Foley balloon and beneath the indwelling catheter can be a natural breeding ground for microbes which can migrate in the body.

Bladder spasms can also occur with an indwelling catheter which causes the bladder to cease its normal cycle of filling and flushing. A dynamic functioning system is converted to a static state with a catheter, and painful bladder spasms can occur. Bladder atone can also occur where short term or more permanent loss of natural bladder functions occurs by using a catheter.

It is also generally well known in medical circles that a human body's primary defense mechanism against urinary tract infections and the other problems listed above is the process known as "wash-out", where it is advantageous to allow a bladder to normally fill up and be released periodically at one time(all at once) rather than in an uncontrolled drip fashion that would occur with using a traditional catheter. See Cecil, Textbook of Medicine, Saunders Co. 18th Edition, Page 866, 1988; and Kunin editorial, New England Journal of Medicine, Vol. 319, No. 6. 1988.

Various catheter type instruments and procedures have been used for draining bladders of patients in hospitals. These instruments and procedures have evolved from constant (non-cycling) drip drainage through painfully inserted catheters by siphoning, suction and various types of awkward manually externally controlled cycling apparatus and procedures. Fundamental to an effective, safe, and appropriate device and method is allowing the bladder to fill reasonably and then draining it without a suction pump and without allowing build-up or entry of infectious contaminants in the drainage system.

U.S Pat. Nos. 2,602,448 and 2,860,636 use siphons in combination with reservoirs to provide cyclic draining of the bladder and pressure release is controlled by raising the height of the device on a bedside tree. These devices are subject to distortion by shifting and turning of the patient and are unreliable (can compromise safety) and restrict patients.

U.S. Pat. No. 3,598,124, describes a siphon leg controlled by attaching a catheter to a bedside tree at predetermined heights, to vary the pressure to drain the bladder with a flutter valve to break the siphon action of the system once the bladder has drained.

U.S. Pat. No. 4,230,102, describes a device for the draining of a bladder in which a T-joint has been placed on a catheter and has a pressure membrane attached thereto in a large casing for actuating a pressure switch which in turn actuates an electric motor driving a gear train and cam. A cam follower is spring loaded to clamp the catheter for two minute cycles upon actuation by the pressure switch to drain the bladder. These types of devices, can be expensive, bulky and positions an electricity source close to the catheter and the patient.

U.S. Pat. No. 4,424,058, describes a spring-return valve in conjunction with a siphon-release orifice to prevent both excessive suction and urine from remaining in the system after drainage. A problem with this system was that the restoring force of the spring increased with distance of travel from a closed position. The valve is unsatisfactory because it closed again as soon as the urine fluid pressure dropped off, thus causing fluid to remain trapped in the bladder to stagnate with further elapsed time. Only a full bladder would open it, sometimes at an uncomfortably high (and potentially unsafe) pressure, and then it closed too soon to allow complete drainage unless overridden by the patient bearing down heavily on the lower abdomen. Also, the tube positioning provided a situation for retention of fluid in the system.

U.S. Pat. Nos. 4,865,588 and 5,114,412 to Flinchbaugh, the inventor of the subject invention, describe "magnetic bladder cycler", title, that requires a "magnet" sliding within a passageway to close a valve port and may use springs and the like, for enhancement. These devices must be added on as, or after, someone is catheterized and is mounted external the catheter. These devices use components substantially larger than a standard diameter of a catheter, thus taking up more space, is more obtrusive, more labor intensive.

None of the proposed patented devices and techniques described above solve all the problems with catheters that are listed above.

SUMMARY OF THE INVENTION

A primary objective of the invention is to provide an indwelling catheter that does not stretch out the urethra when being used and can conform to a closed urethra.

A secondary objective of the invention is to provide an indwelling catheter that does not require extra inflation lines for inflating a balloon end nor an inflatable portion.

A third objective of the invention is to provide an indwelling catheter that is less painful and safer when being used than balloon tipped or inflatable catheters.

A fourth objective of the invention is to provide an indwelling catheter that reduces or eliminates the need for medications, sedatives and narcotics as compared to using balloon tipped or inflatable catheter.

A fifth objective of the invention is to provide a catheter having a low pressure magnetic valve for bladder management cyclic flow control. As long as any fluid is coming through the line, the valve will remain open until a complete emptying of the bladder is achieved.

A sixth objective of the invention is to provide catheter having a low pressure magnetic valve for bladder management cyclic flow control that establishes complete and sterile drainage as the bladder is being emptied.

A seventh objective of the invention is to provide a catheter having a low pressure magnetic valve for bladder management cyclic flow control that can be automatically run with a simple and convenient manual override that can be selectively engaged.

An eighth objective of the invention is to provide a catheter having a low pressure magnetic valve for bladder management cyclic flow control that helps restore normal body functions of bladder filling and emptying in a cyclic manner, with normal, healthy pressure sensations in spite of the presence of the catheter which traditionally inhibits "natural" drainage.

The ninth objective of the invention is to provide a catheter having a low pressure magnetic valve for bladder management cyclic flow control which can reduce and eliminate known catheter causing problems such as urinary tract infections, struvite crystal encrustation, bladder spasms and bladder atone.

The tenth objective of the invention is to provide a catheter having magnetic or electret valves that can be used inside of catheter tube for bladder management cycling.

The eleventh objective of the invention is to allow a user wearing a catheter to use their bladder detrusor muscle assist to selectively turn on a valve in the catheter and complete an entire urination emptying cycle of their bladder.

The twelfth objective of the invention is to provide a self sealing sampling port that can be located on the bladder management cycling valve.

The expandable and collapsible catheter includes a catheter tube having a head member with downwardly projecting hollow sleeve with interior and exterior threaded walls inside the catheter, exterior longitudinal slits in the catheter tube, and fixed internal ring having reverse threaded interior walls, within the tube beneath the slits. A user can insert one end of a wire or small-diameter flexible plastic rod type stylette having a threaded tip end through the catheter tube until the threaded tip is screwed in a clockwise direction within the threaded interior walls of the head member. The bottom end of the stylette remains exposed and outside the lower end of the catheter tube. Next the upper head member end of the catheter can be inserted into the bladder through the urethra and positioned in place. The medical practitioner can pull down on the exposed end of the styllete causing the portion of the catheter with the longitudinal strips to expand outward into wing configurations causing, or allowing for, the catheter to be held in an indwelling position within the bladder. Next, the medical practitioner can rotate the stylette in a counter-clockwise direction releasing the threaded end of the stylette from the interior threads of the sleeve in the head member, simultaneously screwing the exterior threaded walls of the sleeve into the interior threaded sleeve of the fixed ring member, thus locking the head member to the ring member while keeping the longitudinal strips in an expanded and folded out positions. The stylette is then removed before the catheter is used for drainage resulting in less pain to the patient, less stretching of the urethra and elimination of problems associated with prior art catheters.

Other embodiments of the invention provide for either consistent magnetic or electret opening and closing of a valve seal with decreased, rather than increased, closing pressure when being opened. As the bladder is being emptied, the decreasing of head pressure against the valve can keep the valve open to establish a complete and sterile drainage. Magnetic and electret valves can be inside the catheter and thin enough to not obstruct fluid flow.

In the invention, valve-closing pressure can decrease as a result of three important factors: (1) magnetic pull of a valve decreases as its open distance from magnetic attraction increases, (2) the gravity-enhanced fluid flow column in the drain down tube provides a slight negative pressure on the back side of the cycling valves (thus tending to hold the valve open until the drain tube empties completely), and (3) fluid passing through the system provides a partial mass flow insulation which tends to hold the cycling valves open, also decreasing any net magnetic or electro static attraction between valve members.

The very low-pressure valve system of the invention allows safe and proper operating pressures, maximum fluid flow rate and complete drainage of the system.

The use method described here is medical in nature, applying to bladder drainage of catheterized patients into a urine collection bag, as needed, in a normal, cyclic fashion. In other words, head pressure of urine building up in volume against the detrusor muscle of a bladder and in a catheter running from the bladder to the valve where it is positioned on a patient's leg or rests on the bed sheet, causes the valve to open away from the valve-port seat. When the valve is opened, distance increases between the valve magnetic member and a member to which it is magnetically attracted in the direction of the valve-port wall, thereby allowing the valve to remain open with less pressure than that initially required to open it. Fluid passing between the open valves which it is attracted magnetically or by electrets decreases further still the closing pressure to offset the head-pressure opening of the valves.

The entire valve system (in the embodiment of a small, streamlined, compact, integrated and durable devices) also serves as an anti-reflux valve between the patient and the urine collection bag, thus preventing drained (and possibly old and unsterile, septic, contaminated) urine from ever re-entering the catheter, urethra, and bladder of the patient, and potentially causing infection or other problems.

The invention can use a manual override for the valves by selectively distancing an externally positioned magnetic members or electret members from the valves that are attracted to it. The override gives flexibility of pressure adjustment and provides the opportunity of assuring full drainage when desired by either physician or the patient. This could manifest itself, in the event of excessive discharge of viscous matter or other mode of lumen blockage, as a "safety" valve to relieve fluid pressure buildup.

The invention can be used as a hospital instrument whenever an indwelling catheter is required, or in clinics, or in physician's offices, or in homes for draining urine from bladders of patients automatically and safely after normal filling, thoroughly and antiseptically. This use is in strong contrast to the typical, non-cyclical, continuous drip associated with urethral catheter drainage into a collection bag. The use of the invention with catheterized patients can help some patients with bladder "retraining" to restore the more normal body function of bladder filling and emptying in a cyclic manner, with normal, healthy pressure sensations in spite of the presence of the catheter which here-to-fore prevented "natural" bladder drainage.

A modified urocycler attachment with self-sealing sampling port can be attached to an outer end of most any popular catheter tube. The invention can use extra thin walled catheters, and anti-microbial materials.

Further objects and advantages of this invention will be apparent from the following detailed description of a presently preferred embodiment which is illustrated schematically in the accompanying drawings.

BRIEF DESCRIPTION OF THE FIGURES

FIG. 5 shows another view of FIG. 4 with the tip end of the stylette passing through the ring member of the catheter.

FIG. 6 shows another view of FIG. 5 with the tip end of the stylette located between the ring member and the head member within the catheter.

FIG. 7 shows a cross-section of the stylette, catheter, ring and head members of FIG. 6.

FIG. 8 shows another view of FIGS. 6–7 with the stylette screwing into the downwardly protruding hollow threaded tip end of the head member.

FIG. 9 shows another view of FIG. 8 with the tip end of the stylette attached to the head member of the catheter.

FIG. 10 shows a cross-sectional view of FIG. 9.

FIG. 11 the head member of FIGS. 9–10 after being pulled in the direction of arrow P1 toward the ring member 80.

FIG. 12 is a cross-sectional view of FIG. 11.

FIG. 13 is another view of the head member of the stylette of FIGS. 11–12 being pulled in the direction of arrow P2 in a final compressed position.

FIG. 14 is a cross-sectional view of FIG. 13.

FIG. 15 shows the novel catheter of preceding figures after being inserted into the urethra portion of a bladder.

FIG. 16A shows another view of the catheter in the bladder of FIG. 15 with the wing portions of the catheter engaged within the bladder.

FIG. 16B is an enlarged view of the expanded wing portions of the catheter of FIG. 16A.

FIG. 16C is a cross-section of the urethra and catheter of FIG. 16A in a drainage state.

FIG. 16D is another cross-section of the urethra and catheter of FIG. 16A in a collapsed non drainage state.

FIG. 17 is a cross-sectional view of a magnetic cycling piston valve in a closed position in a catheter for controlling bladder drainage.

FIG. 18A is another view of the valve of FIG. 17 in an open position.

FIG. 18B is a top view of the valve of FIG. 18A along arrow 18B.

FIG. 19 is a cross-sectional view of magnetic cycling funnel/flap valve in a closed position within a catheter for controlling bladder drainage.

FIG. 20 is another view of the valve of FIG. 19 in an open position.

FIG. 21 is a cross-sectional view of an electret cycling valve in a closed position within a catheter for controlling bladder drainage.

FIG. 22 is another view of the valve of FIG. 21 in an open position.

DESCRIPTION OF THE PREFERRED EMBODIMENTS

Before explaining the disclosed embodiments of the present invention in detail it is to be understood that the invention is not limited in its application to the details of the particular arrangement shown since the invention is capable of other embodiments. Also, the terminology used herein is for the purpose of description and not of limitation.

This invention is a Continuation-In-Part of U.S. application Ser. No. 10/010,534 filed Dec. 7, 2001, which is incorporated by reference.

Expanding End of Catheter with Stylett Embodiment

Figure 2:
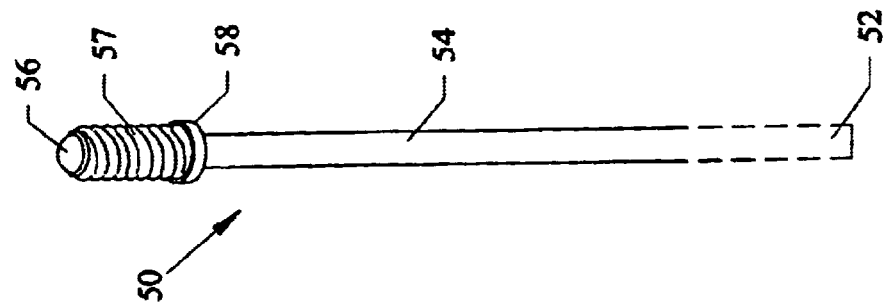
FIG. 2 shows a stylette with upwardly protruding threaded tip for use with the invention.

FIG. 2 shows a stylette 50 with an upwardly protruding tip end 56 having a threaded upper surface 57 and upper surface base portion 58 that can be used with the subject invention. Stylette 50 can include a longitudinal portion 54, and a lower end 52 that can be grabbed by the practitioner using the stylette 50. The Stylette 50 can be formed from a semi-rigid wire type material such as but not limited to metal wire, plastic, combinations, thereof, and the like.

Figure 3:
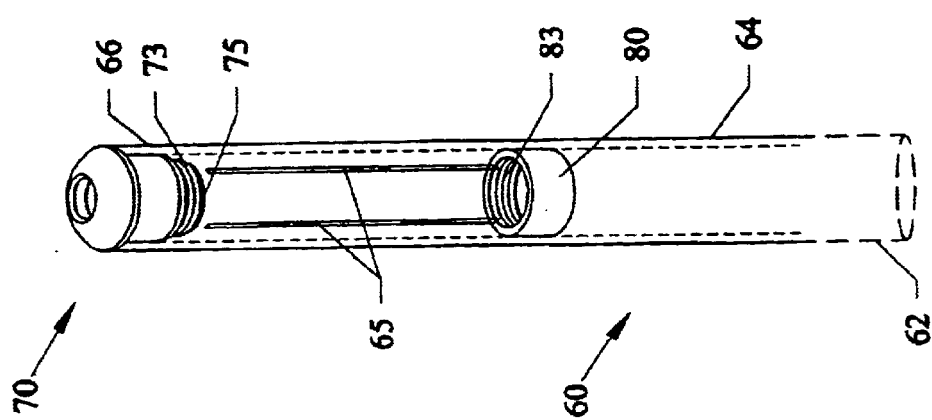
FIG. 3 shows a catheter having exterior slit(s) and with head member having downwardly protruding threaded portion and fixed interior ring member having interior threads.

FIG. 3 shows a catheter 60 having exterior slit(s) 65 and with head member portion 70 in the upper end 66 of the catheter 60 having downwardly protruding threaded portion and fixed interior ring member 80 having interior threads 83.

Figure 4:
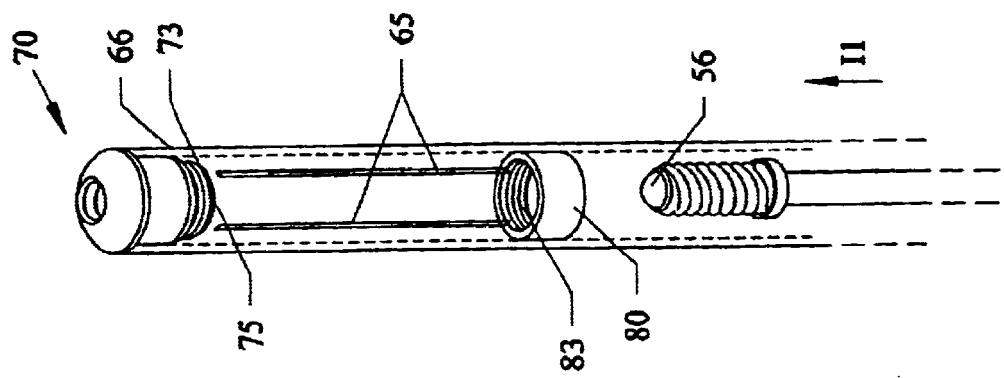
FIG. 4 shows the stylette of FIG. 2 being inserted into the catheter of FIG. 3.

FIG. 4 shows the stylette 50 of FIG. 2 being inserted into the catheter 60 of FIG. 3 and moved in the direction of arrow I1. FIG. 5 shows another view of FIG. 4 with the tip end 56 of the stylette 50 being moved in the direction of arrow I2, passing through the ring member 80 of the catheter. FIG. 6 shows another view of FIG. 5 with the tip end 56 of the stylette 50 located between the ring member 80 and the head member 70 passing in the direction of arrow P3 within the catheter 60. FIG. 7 shows a cross of the stylette 50, catheter 60, ring member 80 and head member 70 of FIG. 6.

FIG. 8 shows another view of FIGS. 6–7 with the tip end 56 and threaded portion 57 of the stylette 50 screwing into the downwardly protruding hollow threaded tip end 75 of the head member 70 in the catheter 60 by rotating in a clockwise direction R1.

FIG. 9 shows another view of FIG. 8 with the tip end base portion 58 of the stylette 50 attached to the head member 70 of the catheter 60, where the base portion 58 having a wider diameter than the outer diameter of the inwardly facing threaded portion 77 that it abuts against the lower portion thereof. FIG. 10 shows a cross-sectional view of FIG. 9. Referring to FIGS. 9–10, the head member 70 can include two parts a partially freely rotatable portion 71, 74, 77, and a fixed ring portion 78 the latter of which can be fixably attached(adhered) to the inner walls of the upper end 66 of the catheter tube 60. Upper and lower ledges 71, 77 allow for some rotation of central member 71, 72, 74, and 77.

During use of the novel catheter assembly, the catheter 60 with internal attached stylette 50 can be inserted into a urethra portion of the bladder of a patient that is going to be catheterized (which will be described in detail in reference to FIGS. 15, 16A–16C).

FIG. 11 the head member 70 of FIGS. 9–10 after being pulled by the base portion 52 of the stylette 50 in the direction of arrow P1 toward the ring member 80. FIG. 12 is a cross-sectional view of FIG. 11. The slits (65, 66 shown in FIGS. 3–4) in the sides of the catheter 60 expand outward and form wing portions 68

FIG. 13 is another view of the head member 70 of the stylette 50 of FIGS. 11–12 being pulled in the direction of arrow P2 in a final compressed position. FIG. 14 is a cross-sectional view of FIG. 13. The stylette 50 can be rotated in a counter-clockwise direction as shown by arrow R2, allowing the lower external threaded surface 73 of the head member 70 to rotate within the internal threaded walls 83 of ring member 80, the latter of which is fixably attached to the inside of the catheter tube 60. After the head member 70 as become lockably attached to ring member 80, the upper threaded tip portion 57 of the stylette 50 can be further rotated in the direction of arrow R2 allowing the stylette 50 to become separated from the both the head member 70 and ring member 80 and then pulled in the direction of arrow P3 out from the opposite end 62 of the catheter tube 60.

FIG. 15 shows the novel catheter 60 of preceding figures after being inserted into the urethra portion 14 of a bladder 10. Here, the stylette 50 is part of the catheter 60.

FIG. 16A shows another view of the novel catheter 60 in the bladder of FIG. 15 with the wing portions 68' of the catheter 60 expanded within the bladder. FIG. 16B is an enlarged view of the expanded wing portions 68' of the catheter 60 of FIG. 16A. As previously described in reference to FIGS. 13–14, the stylette 50 is removed before the catheter tube 60 is used for bladder drainage status.

FIG. 16C is a cross-section of the urethra 14 and catheter 60 of FIG. 16A while the catheter tube 60 is being used in a drainage state. As shown the urethra 14 is temporarily in an open fluid passage state.

FIG. 16D is a cross-section of the urethra 14 and catheter tube 60 of FIG. 16A while the catheter tube 60' is in a collapsed non drainage state within the urethra 14'. The catheter tube 60' conforms to a closed passageway 15' of closed urethra 60'.

Figures 1A, 1B:
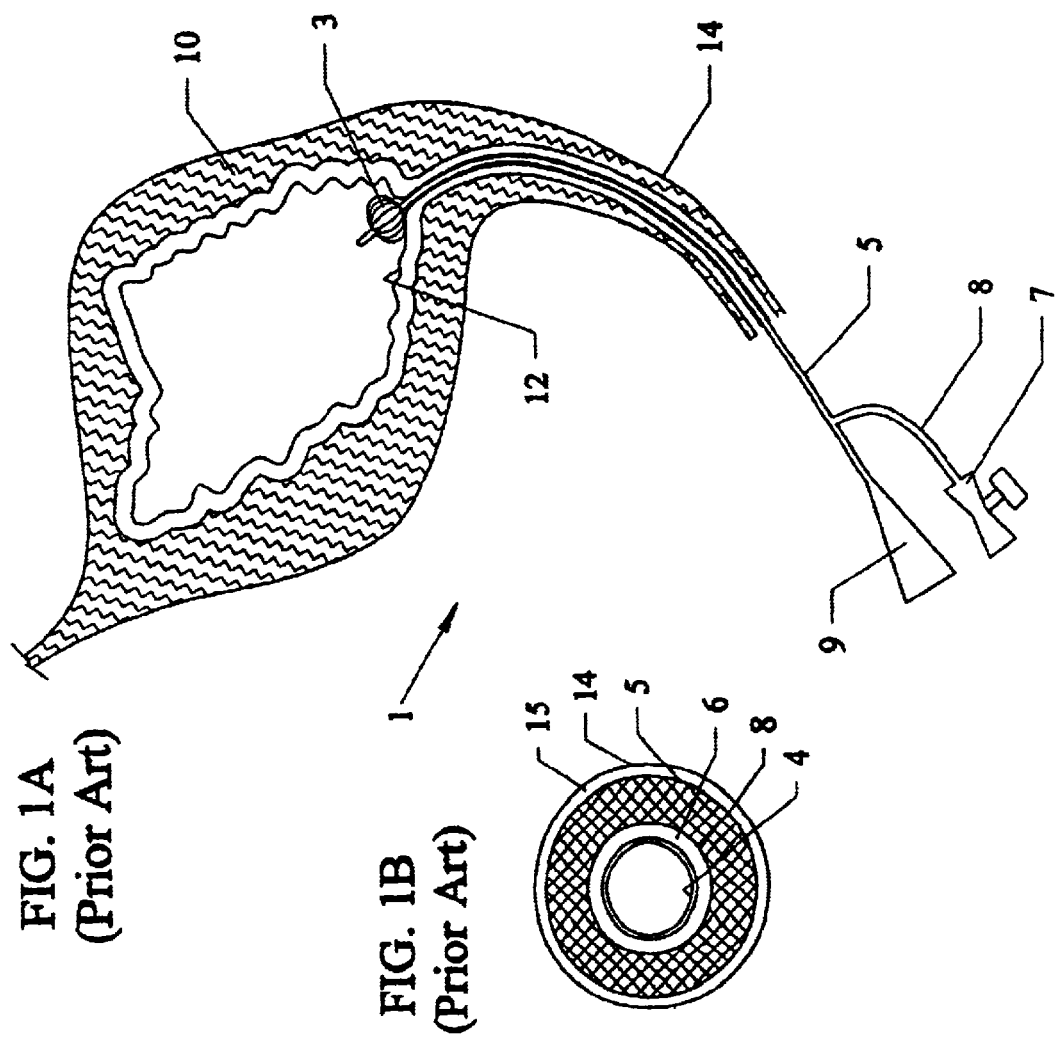
FIG. 1A shows a prior art indwelling Foley type catheter with a balloon tipped end.
FIG. 1B is a cross-sectional view of the catheter of FIG. 1A within the urethra passage.

Referring to FIGS. 16C–16D, these views further detail the thinner catheter tube 60 that can be used instead of the thick walled catheter tube (5 shown in FIG. 1B) of the prior art. The novel catheter tube can have an outer diameter of approximately ¼ of an inch with a wall thickness of approximately 0.0055 inches, thus allowing for almost an approximate ¼ inch inner diameter flow through portion for the catheter tube 60. Unlike the thick walled limited drainage passageways, of the prior art, the novel catheter tube 60 more closely approximates the natural diameter size passageway 15 of the urethra 14.

Additionally, unlike the prior art, the novel catheter 60 of the subject invention can conform to a closed passageway 15' of a closing state urethra 60'. Thus, the subject invention does not continuously stretch the urethra, nor cause continuous pain to the catheterized patient, nor cause all the other negative effects by known types of catheters that were described in the background section of the subject invention.

Magnetic Cycling Valves

FIG. 17 is a cross-sectional view of a first embodiment 100 of a magnetic cycling piston valve 130 in a closed position in a catheter 60 for controlling bladder drainage. FIG. 18A is another view of the valve 130 of FIG. 17 in an open position. FIG. 18B is a top view of the retainer 132 of the valve 130 of FIG. 18A along arrow 18B.

Referring to FIGS. 17 and 18A–18B, an upper nonmagnetic ring member 110 such as flexible plastic, and the like, can be fixably attached to an inner wall 61 of the catheter tube 60, the latter of which can be the catheter tube 60 described in reference to the preceding figures. Lower ring 120 can be a flexibly pliable permanent magnetic ring hat is fixably attached to the inner wall 61 of the catheter tube 60 beneath the nonmagnetic ring 110. The moveably piston 130 can include a thin retainer portion 132 such as a single perpendicular portion having one or two ends which can rest on the top 112 of upper ring 110. As shown in FIG. 18B, the retainer 132 is thin enough to allow fluid to pass about the retainer through the openings defined by the ring members 110, 120. The ring member 110, 120 used can have thin wall thicknesses so as not to obstruct the passageway formed by the inner walls 61 of the catheter tube 60. Attached perpendicular to and extending below retainer 132 can be a thin longitudinal shaft 134 such as a flexible plastic strip, and the like. Attached beneath shaft 134 can be a stopper 136 formed from a magnetic material that is attracted to lower magnet ring 120, or a metal material that is attracted to lower magnetic ring 120, and the like. Alternatively, the stopper 136 can be a magnetic material and the lower ring member 120 can be a metal material that are attracted to each other. Inwardly slanting sides 137 on the stopper 136 can allow for the stopper 136 to be substantially sealed against the opening in lower ring member 120.

Referring to FIGS. 17 and 18A–18B, in operation fluid flowing in the direction of arrow F1 can push the stopper 136 in a downward direction as shown by arrow M1 causing the stopper 137 to separate from the lower ring member 120. The magnetic attraction of the lower ring member 120 and stopper 132 can be calibrated to be approximately equal to natural bladder drainage pressure flows. For example, approximately 0.1 ounces per square feet or approximately 15 cm height of H2O fluid in the catheter tube 60 can be calibrated to be enough to push open the seated stopper 36 of FIG. 17 to the positions shown in FIG. 18A.

FIG. 19 is a cross-sectional view of a magnetic cycling embodiment 200 using a funnel/flap valve 201 in a closed position within a catheter 60 for controlling bladder drainage. FIG. 20 is another view of the valve 201 of FIG. 19 in an open position.

Referring to FIGS. 19–20, magnetic valve embodiment 200 can include a pliable thin walled ring member 210, such as pliable plastic and the like, fixably attached to an inside wall portion 61 of the novel catheter tube 60. Attached to an extending downward from the ring member 210 can be funnel portions 220, 230 that can be formed from two thin pliable flaps having a lower end portions with small pliable type magnets 225, 235 attached thereto that be attracted to each other closing off the passageway formed from the opening through ring member 210 which can give the appearance of a funnel shape, and the like. Alternatively, the funnel portions 220, 230 can be single pliable cylindrical chamber such as thin walled plastic, a plastic bag, and the like, that can have a wall thickness of approximately 0.001 inches, and the like. Although two magnets 125, 135 are described, the invention can be used with one magnet 125 and a portion 135 having metal attributes and the like. Similar to the preceding embodiment, the ring member 210 and funnel portions 220, 230 can include thin enough walls not to reduce the opening formed by the inner walls 61 of the catheter tube 60. The magnetic attraction of the portions 225, 235 of the funnel portions 220, 230 can be calibrated to be approximately equal to natural bladder drainage pressure flows. For example, approximately 0.1 ounces per square feet or approximately 15 cm height of H2O fluid in the catheter tube 60 pushing in the direction of arrow F2 can be calibrated to be enough to push open the funnel of FIG. 19 to the positions shown in FIG. 20.

Electret Cycling Valve

FIG. 21 is a cross-sectional view of an electret cycling valve embodiment 300 in a closed position within a catheter 60 for controlling bladder drainage. FIG. 22 is another view of the valve 301 of FIG. 21 in an open position. Here a pliable thin walled ring member 310 can be fixably attached to an inner wall surface 61 of catheter tube 60. Extending below ring member 310 can be two electret material sheets 320, 330 such as flexible plastic sheets imbedded with electric charges. For example, sheet 320 can include a positive charge on the inner surface of lower end 322 and sheet 330 can include a negative charge an inner surface of lower end 332. Similar to the preceding embodiment the sheets 320, 330 can form a funnel shape that can open and close the passageway formed by inner walls 61 of the catheter tube 60. The electret attraction of the portions 322, 332 of the funnel portions 320, 330 can be calibrated to be approximately equal to natural bladder drainage pressure flows. For example, approximately 0.1 ounces per square feet or approximately 15 cm height of H2O fluid in the catheter tube 60 pushing in the direction of arrow F3 can be calibrated to be enough to push open the funnel of FIG. 21 to the position shown in FIG. 22.

External Urocycler Embodiment

Figure 23:
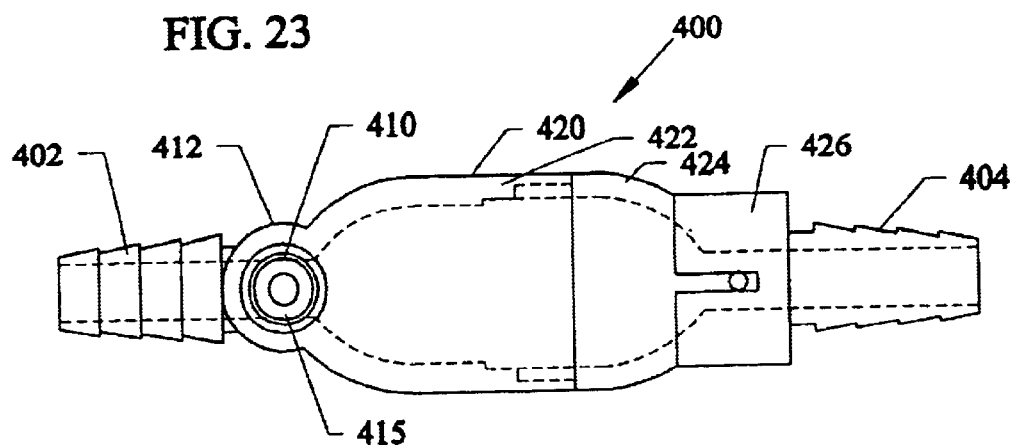
FIG. 23 shows a top view of an urocycler embodiment for use with the novel catheter tube.
Figure 24A:
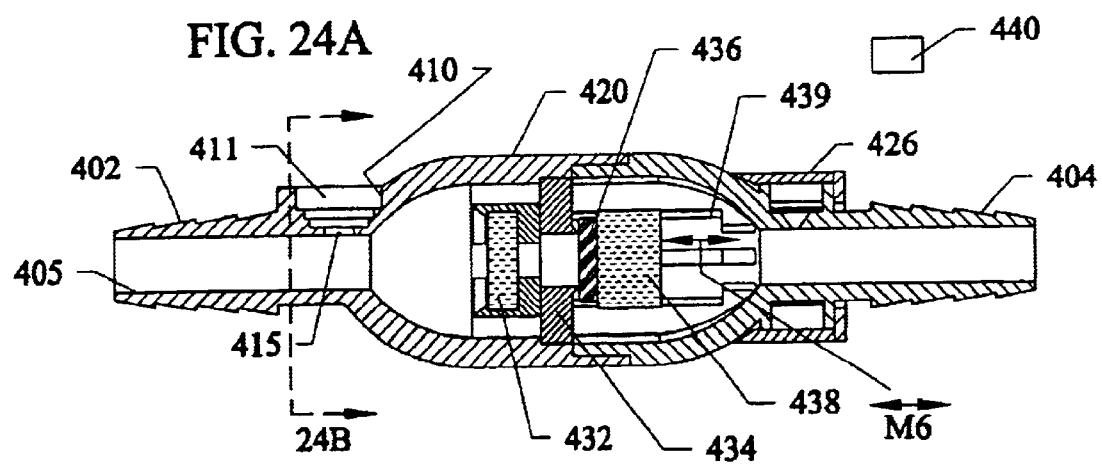
FIG. 24A is a side cross-sectional view of the urocycler embodiment of FIG. 23.
Figure 24B:
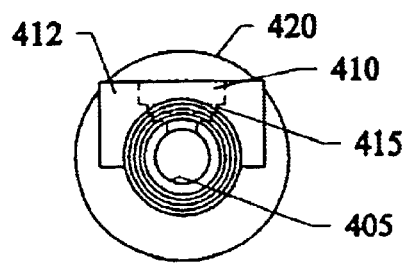
FIG. 24B is a cross-sectional view of the embodiment of FIG. 24A along arrow 24B.

FIG. 23 shows a top view of a urocycler embodiment 400 for use with the catheter tube 60 of the preceding figures. FIG. 24A is a side cross-sectional view of the urocycler embodiment 400 of FIG. 23. FIG. 24B is a cross-sectional view of the embodiment 400 of FIG. 24A along arrow 24B.

Embodiment 400 can use the urocycler components described in parent U.S. application Ser. No. 10/010,534 filed Dec. 7, 2001, which is incorporated by reference, and can include inlet barbed connector 402 and outlet barbed connector 404 attached to opposite ends of main nonmagnetic housing 420, the latter of which can have a male pronged end 424 which snapably and sealingly attaches to a female prong end 422. A vent hole port 426 can be located on the downstream end of male housing portion 424. Inside the upstream portion 422 of housing 420 can be a fixed valve member 432 being formed of a magnetic member, and the like, fixed in position adjacent to a hollow valve port ring 434 whose center flow passageway can be opened and closed by moveable valve member 438 with resilient valve seat 436 which can move forward and backward in the direction of double arrow MG along inner channel rails 439 so as to open and close the valve in a cycling manner similar to those embodiments previously described.

A manual override for the valves can be accomplished by selectively distancing an externally positioned magnetic member 440 from the moveable magnet member 438. The override gives flexibility of pressure adjustment and provides the opportunity of assuring full drainage when desired by either physician or the patient. This could manifest itself, in the event of excessive discharge of viscous matter or other mode of lumen blockage, as a "safety" valve to relieve fluid pressure buildup. This override feature can be used with the previous embodiments by using either an external magnet or an external electret member.

This urocycler embodiment can include a novel sampling port 410 formed about a port housing 412, with an inner port surface having with inwardly protruding steps 415 so that a like sized and fitted elastomer shaped plug member 411 can be mateably attached thereto. Port 410 can include an elastomer plug shape that is continuously self-sealing after being punctured by needles and the like. In operation, a practitioner can attach the inlet barbed connector 402 to the exposed lower conical shaped end (69 for example in FIG. 15) of the catheter tube 60, and the barbed outlet port 404 of embodiment 400 to a collection bag, and the like. During a urine drainage cycle, the practitioner can swab the outside surface of the elastomeric plug shaped membrane 410 with an antiseptic, and the like. A needle(cannula) or syringe or other sampling device can be inserted through the center of the sampling port 410 and a fresh sample of urine can be drawn. After which, the syringe/cannular can be withdrawn, the self-sealing elastomeric plug becomes sealed again, and the sampling port 410 can be swabbed with antiseptic.

Anti-microbial Catheter Materials

The catheter can include an anti-microbial surface such as an interior coating and/or outside coating. Alternatively, the ant-microbial surface can be caused from an impregnated material which leaches to either or both the inside and/or the outside of the catheter tube. The anti-microbial surface and be an anti-bacterial material, and/or a hydrophyllic material that is compatible with the skin and will not support bacterial growth. Materials that can be used include but are not limited to silver alloy, and the like.

Although the catheter tube 60 is described as being used with the magnetic cyclers of the preceding figures, the novel magnetic cyclers can be used inside other types of catheter tubes such as those described in the background section of the invention.

Although the invention describes the catheters for use as a suprapubic type by passing through the urethra, the invention can be used with other types of catheter uses such as but not limited to renal catheters, cardiology catheters, and the like.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. An indwelling catheter, comprising:
   a catheter tube having an upper end and a bottom end with an expandable portion adjacent to the upper end;
   longitudinal means for being inserted into the catheter tube having a top end which can attach to the upper end of the catheter tube, and a lower end adjacent to the bottom end of the catheter tube, wherein pulling on the lower end of the longitudinal means causes the expandable portion of the catheter tube to expand inside of a space;
   a head member in the upper end of the catheter tube having a downwardly projecting threaded portion;
   a sleeve fixably held inside the catheter below the expandable portion;
   means for attaching the upper end of the catheter tube to the sleeve after the upper end is pulled to the sleeve;
   a threaded wall on the sleeve for rotatably screwing about the downwardly projecting threaded portion of the head member;
   means for supporting the head member in at least one rotatable position relative to the catheter tube; and
   a threaded tip end on the longitudinal means for mateably screwing to the threaded portion of the head member.

2. The catheter of claim 1, wherein the expandable portion includes:
   wings which expand outward.

3. The catheter of claim 1, wherein the catheter tube further comprises:
   at least one longitudinal slit adjacent the upper end of the catheter tube.

4. The catheter of claim 1, wherein the catheter tube further comprises:
   an anti-microbial surface, the surface being selected from at least one of: a surface coating and an impregnated material.

5. A passive cycling control for catheters, comprising:
   a magnetic valve inside a catheter tube, the magnetic valve having a closed position for obstructing flow through the catheter tube and an open position for allowing flow therethrough, the magnetic valve including a ring having a opening therethrough and a shaft having a head end and a foot end, the shaft for moving within the opening of the ring between a first position where the head end abuts against an upper portion of the ring closing an upper end of the opening and the foot end of the shaft abuts against a lower portion of the ring closing a lower end of the opening, and wherein one of the ring and the foot end contains a magnet; and
   non-inflatable holding means for supporting an upper end of the catheter within a bladder, wherein bladder pressure causes the magnetic valve to cycle between the closed position and the open position to replicate natural cycling conditions of drainage of the bladder.

6. The cycling control of claim 5, further comprising:
   an anti-microbial surface on the catheter, the surface being selected from at least one of: a surface coating and an impregnated material.

7. A drainage cycler for use with catheters, comprising in combination:
   a catheter tube;
   a low pressure-activated valve attached to the catheter tube, wherein pressure applied to the pressure-activated valve allows for the valve to cycle between an open and a closed position by a patient's detrusor muscle, the valve including an electret valve sized to be positioned inside the catheter; and
   a self-sealing sampling port adjacent to the valve for allowing samples of fluid to be safely removed while the catheter tube is filled with fluid.

8. The cycler of claim 7, wherein the magnetic valve includes:
   a housing with a connector for being attached to an exposed end of the catheter tube.

9. The cycler of claim 7, wherein the catheter tube includes:
   an anti-microbial surface.

10. A passive cycling control for catheters, comprising:
    a magnetic valve inside a catheter tube, the magnetic valve having a closed position for obstructing flow through the catheter tube and an open position for allowing flow therethrough, the magnetic valve including a downwardly narrowing funnel shape having a large top open end which narrows down to a magnetic valve end which opens and closes upon the pressure from the bladder; and
    non-inflatable holding means for supporting an upper end of the catheter within a bladder, wherein bladder pressure causes the magnetic valve to cycle between the closed position and the open position to replicate natural cycling conditions of drainage of the bladder.

11. A passive cycling control for catheters, comprising:

an electret valve inside a catheter tube, the electret valve having a closed position for obstructing flow through the catheter tube and an open position for allowing flow therethrough; and non-inflatable holding means for supporting an upper end of the catheter within a bladder, wherein bladder pressure causes the electret valve to cycle between the closed position and the open position to replicate natural cycling conditions of drainage of the bladder.

12. The cycling control of claim 11, wherein the electret valve includes:

an downwardly narrowing funnel shape having a large top open end which narrows down to a electret valve end which opens and closes upon pressure from the bladder.

* * * * *